(12) United States Patent
Smith

(10) Patent No.: US 11,179,566 B2
(45) Date of Patent: Nov. 23, 2021

(54) FITTING METHOD USING CHANNELS

(71) Applicant: Cochlear Limited, Macquarie University (AU)

(72) Inventor: Zachary Mark Smith, Greenwood Village, CO (US)

(73) Assignee: Cochlear Limited, Macquarie University (AU)

(*) Notice: Subject to any disclaimer, the term of this patent is extended or adjusted under 35 U.S.C. 154(b) by 698 days.

(21) Appl. No.: 14/294,714

(22) Filed: Jun. 3, 2014

(65) Prior Publication Data
US 2015/0343217 A1    Dec. 3, 2015

(51) Int. Cl.
| | | |
|---|---|---|
| *A61N 1/36* | (2006.01) | |
| *A61N 1/05* | (2006.01) | |
| *A61N 1/02* | (2006.01) | |
| *A61N 1/08* | (2006.01) | |

(52) U.S. Cl.
CPC ....... *A61N 1/36039* (2017.08); *A61N 1/0541* (2013.01); *A61N 1/36038* (2017.08); *A61N 1/36146* (2013.01); *A61N 1/025* (2013.01); *A61N 1/08* (2013.01)

(58) Field of Classification Search
CPC .. A61N 1/36032; A61N 1/0541; A61N 1/023; A61N 1/36146; A61N 1/08; A61N 1/36038; A61N 1/36039
USPC .......................................................... 607/57
See application file for complete search history.

(56) References Cited

U.S. PATENT DOCUMENTS

| | | | |
|---|---|---|---|
| 6,289,247 B1* | 9/2001 | Faltys | A61N 1/37247 607/55 |
| 2006/0247735 A1 | 11/2006 | Honert | |
| 2007/0043403 A1* | 2/2007 | Blamey | A61N 1/36038 607/55 |
| 2007/0239228 A1* | 10/2007 | Bradley | A61N 1/0551 607/59 |
| 2009/0149917 A1* | 6/2009 | Whitehurst | A61N 1/36017 607/59 |
| 2010/0198301 A1 | 8/2010 | Smith | |
| 2011/0004274 A1 | 1/2011 | Schleich et al. | |

(Continued)

FOREIGN PATENT DOCUMENTS

| | | |
|---|---|---|
| CN | 101277736 A | 10/2008 |
| CN | 102361666 A | 2/2012 |

(Continued)

OTHER PUBLICATIONS

International Search Report for PCT/IB2015/053985 dated Aug. 28, 2015.

(Continued)

*Primary Examiner* — Jennifer Pitrak McDonald
*Assistant Examiner* — Pamela M. Bays
(74) *Attorney, Agent, or Firm* — Piloff Passino & Cosenza LLP; Martin J. Cosenza

(57) ABSTRACT

A method, comprising, fitting an electrical stimulating device to the recipient, the electrical stimulating device including electrodes implanted in the recipient, the electrical stimulating device being a multipolar electrical stimulating device, wherein the fitting includes simultaneously applying multipolar stimulation to the recipient via the electrodes based on at least two different stimulation channels of the electrical stimulating device.

34 Claims, 10 Drawing Sheets

(56) References Cited

U.S. PATENT DOCUMENTS

2011/0106209 A1    5/2011   Saoji
2011/0288613 A1   11/2011   Smith et al.
2012/0191161 A1    7/2012   van Dijk
2012/0300953 A1   11/2012   Mauch et al.

FOREIGN PATENT DOCUMENTS

CN    103068439 A    4/2013
CN    103347465 A   10/2013

OTHER PUBLICATIONS

Andrej Kral et al., "Spatial resolution of cochlear implants: the electrical field and excitation of auditory afferents," Hearing Research 121, 1998, pp. 11-28, Elsevier.

Office Action in CN Application No. 201580038969.0, dated Nov. 27, 2018.

\* cited by examiner

FITTING METHOD USING CHANNELS

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In accordance with an exemplary embodiment, there is a method of fitting an electrical stimulating device to the recipient, the electrical stimulating device including electrodes implanted in the recipient, the electrical stimulating device being a multipolar electrical stimulating device, wherein the fitting includes simultaneously applying multipolar stimulation to the recipient via the electrodes based on at least two different multipolar stimulation channels of the electrical stimulating device.

In accordance with another exemplary embodiment, there is a method comprising obtaining access to a recipient having a plurality of electrodes of an electrical stimulating device implanted in the recipient, wherein the electrical stimulating device is configured to apply electrical stimulation to the recipient via the plurality of electrodes by activating a plurality of stimulation channels, identifying at least one interacting stimulation channel of the plurality of stimulation channels that interacts with a target stimulation channel of the plurality of stimulation channels during autonomous operation of the stimulating device, creating a fitting channel based on the identified at least one interacting stimulation channel and the target stimulation channel, activating the fitting channel to evoke a stimulation induced percept, and setting at least one of a threshold level or a comfort level for the target stimulation channel based on activation of the fitting channel.

In accordance with another exemplary embodiment, there is a non-transitory computer readable medium having recorded thereon, a computer program for executing at least a portion of a method of fitting an electrical stimulating device including electrodes implanted in a recipient, wherein the electrical stimulating device is configured to apply electrical stimulation to the recipient via the plurality of electrodes, the computer program including code for identifying a recipient specific parameter related to a current level of the stimulating device for a first stimulation channel of a plurality of electrode stimulation channels of the electrical stimulating device by instructing the electrical stimulating device to apply multichannel electrical stimulation to the recipient.

In accordance with another exemplary embodiment, there is a device, comprising a cochlear implant fitted to a recipient, the cochlear implant including a plurality of electrodes configured for implantation into a recipient and configured to apply electrical stimulation to the recipient by activating one or more of a plurality of electrode channels of the device to evoke a hearing percept, wherein the device is configured to control the device to apply electrical stimulation to the recipient by activating a first electrode channel of the plurality of electrode channels to evoke a hearing percept at current levels within a range bounded by at least one of a threshold level or a comfort level, wherein at least one of the respective threshold level current level or comfort level current level is based on empirical data that is based on at least one of a recipient specific respective threshold level or comfort level obtained by simultaneously activating the first electrode channel and a second electrode channel of the plurality of electrode channels.

BRIEF DESCRIPTION OF THE DRAWINGS

Embodiments are described below with reference to the attached drawings, in which.

DETAILED DESCRIPTION

Figure 1:
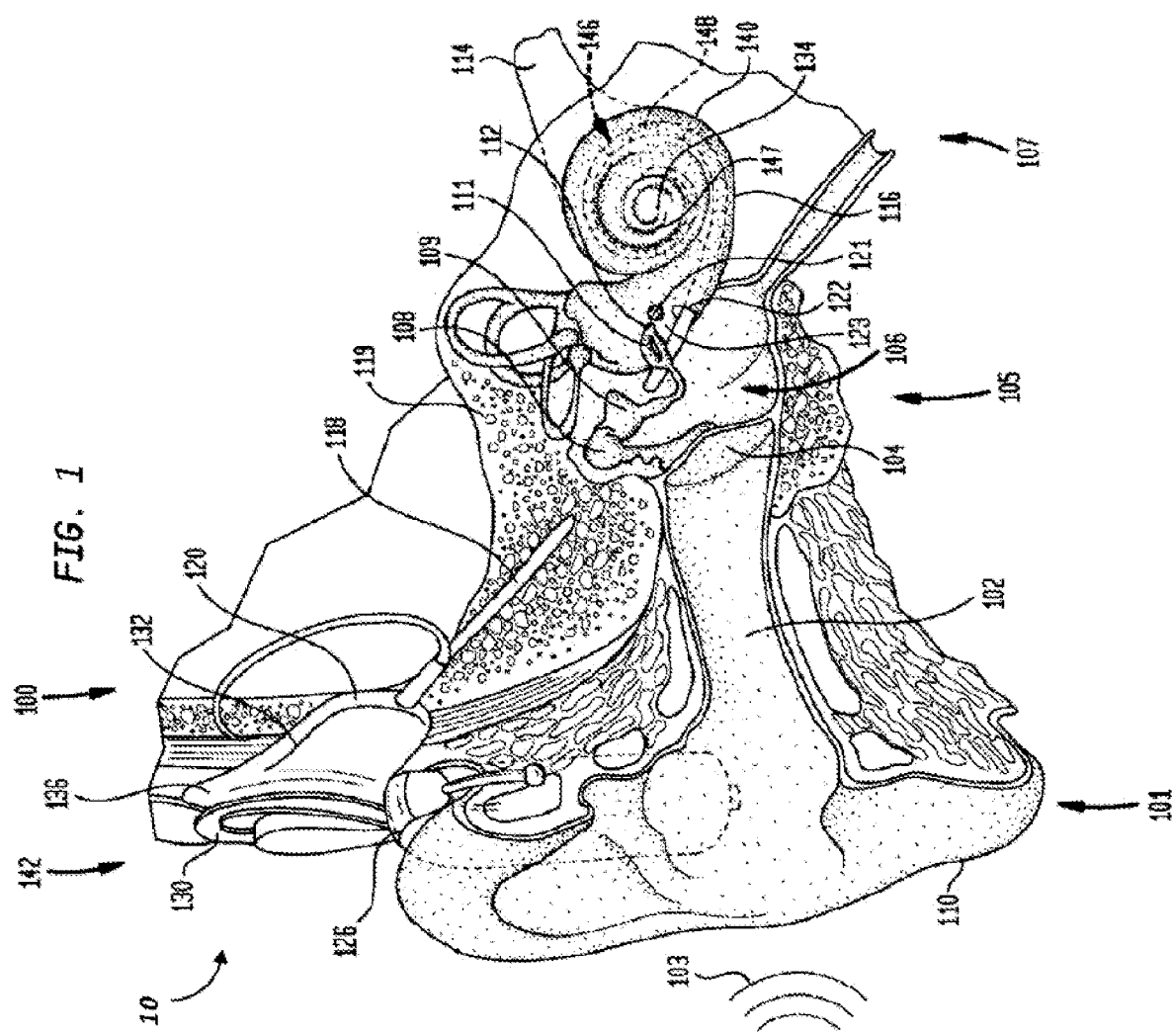
FIG. 1 is a perspective view of an exemplary hearing prosthesis in which at least some of the teachings detailed herein are applicable.

FIG. 1 a is perspective view of a cochlear implant, referred to as cochlear implant 100, implanted in a recipient, to which some embodiments detailed herein and/or variations thereof are applicable. The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery or other energy storage device (e.g., capacitor) that is charged (e.g., recharged) by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Because the cochlea is tonotopically mapped (i.e., spatial locations that are responsive to stimulus signals in a particular frequency range are identified), frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit of the BTE 126 (i.e., specific frequency bands with their associated signal processing paths), are mapped to a set of one or more electrodes to stimulate a desired nerve fiber or nerve region of the cochlea. Such sets of one or more electrodes for use in stimulation are referred to herein as "electrode channels" or "stimulation channels." In at least some exemplary embodiments, each channel has a "base" electrode corresponding to the electrode of the electrode array that is proximate the tonotopically mapped cochlea for a given frequency or frequency range.

Figure 2:
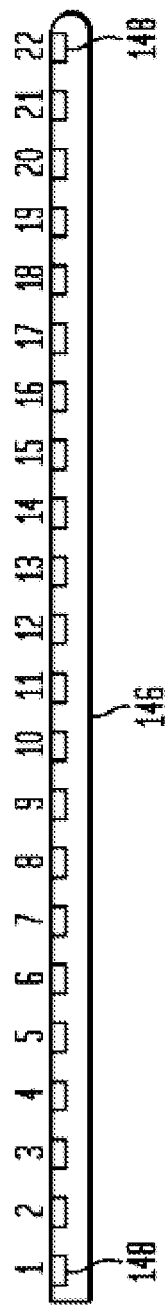
FIG. 2 presents an exemplary electrode array according to an exemplary embodiment.

FIG. 2 illustrates a more detailed view of an exemplary electrode array 146 comprising a plurality of electrodes 148, in accordance with an embodiment. Electrode array 146 may be used to apply different modes of stimulation, such as, for example, monopolar, bipolar, tripolar, or phased-array stimulation. The below discussed embodiments will generally be described with reference to a cochlear implant system in which the electrode array 146 provides complex stimulation channels. As used herein, a complex stimulation channel refers to a stimulation channel that uses three or more electrodes 148, such as, for example, a tripolar stimulation channel or a phased-array stimulation channel. In a tripolar stimulation channel, current flows from one electrode (e.g., electrode 3) and returns to each of two other electrodes (e.g., electrodes 2 and 4). Tripolar stimulation may also be used with an extra-cochlea electrode in which the extra-cochlea electrode (not shown) partially sinks the current flowing from the center electrode (e.g., electrode 3) in conjunction with the two sink electrodes (e.g., electrodes 2 and 4). As will be discussed in further detail below, each of these sink electrodes (e.g., electrodes 2 and 4 and the extra-cochlea electrode) may be weighted so that each sink electrode sinks a percentage of the current flowing from the center electrode (e.g., electrode 3) in accordance with the electrode's assigned weight.

In phased-array stimulation, weights are assigned to a plurality of electrodes (e.g., electrodes 1-5, 2-8, all electrodes, etc.) and the stimulation is applied using the weighted electrodes. Phased-array stimulation may also be used in conjunction with a weighted extra-cochlea electrode (not shown). Phased-array stimulation is discussed by way of example only and not by way of limitation in U.S. patent application Ser. No. 11/414,360 by Chris van den Honert, entitled "Focused Stimulation in a Medical Stimulation Device" and Chris van den Honert and David C. Kelsall, "Focused Intracochlear Electric Stimulation with Phase Array Channels," J. Acoust. Soc. Am., 121, 3703-3716 (June 2007), and the teachings of those documents can be utilized in at least some embodiments of a cochlear implant applicable to the teachings detailed herein and/or variations thereof.

In at least some instances, an audiologist adjusts complex stimulation channel electrode weights of the cochlear implant 100. More specifically, in at least some embodiments, complex stimulation channel weights are adjusted by an audiologist to reduce and/or eliminate simultaneous channel interactions, at least for channels that are more than one base electrode apart from each other. Such exemplary methods of doing so are detailed in U.S. Patent Application Publication No. 2010/098301 (hereinafter, the "'301 publication"). Accordingly, in an exemplary embodiment, the teachings of the '301 publication and/or variations thereof are executed to assign and adjust complex stimulation channel electrode weights of the cochlear implant. Then, in at least some embodiments, the cochlear implant 100 is configured such that respective stimulation channels of the cochlear implant 100 have those respective weights. This can be done, for example, by programming the cochlear implant 100 or by any other process that sets the channels of the cochlear implant 100 to have those weights. This is followed by a fitting process to determine threshold and comfort levels for the stimulation channels as will now be detailed. That said, in an alternate embodiment, the cochlear implant 100 is not programmed or otherwise configured such that the channels of the cochlear implant 100 have those weights before implementing the fitting process. Instead, the weights of the respective stimulation channels are stored in the fitting system (discussed below) used to fit the cochlear implant 100 and the fitting process is then performed, and the cochlear implant 100 is configured such that the respective stimulation channels have the respective weights at some point after the beginning of the fitting method. Any arrangement of the cochlear implant 100 and/or other equipment/devices that will enable the teachings detailed herein and/or variations thereof to be practiced can be used in at least some embodiments.

Figure 3:
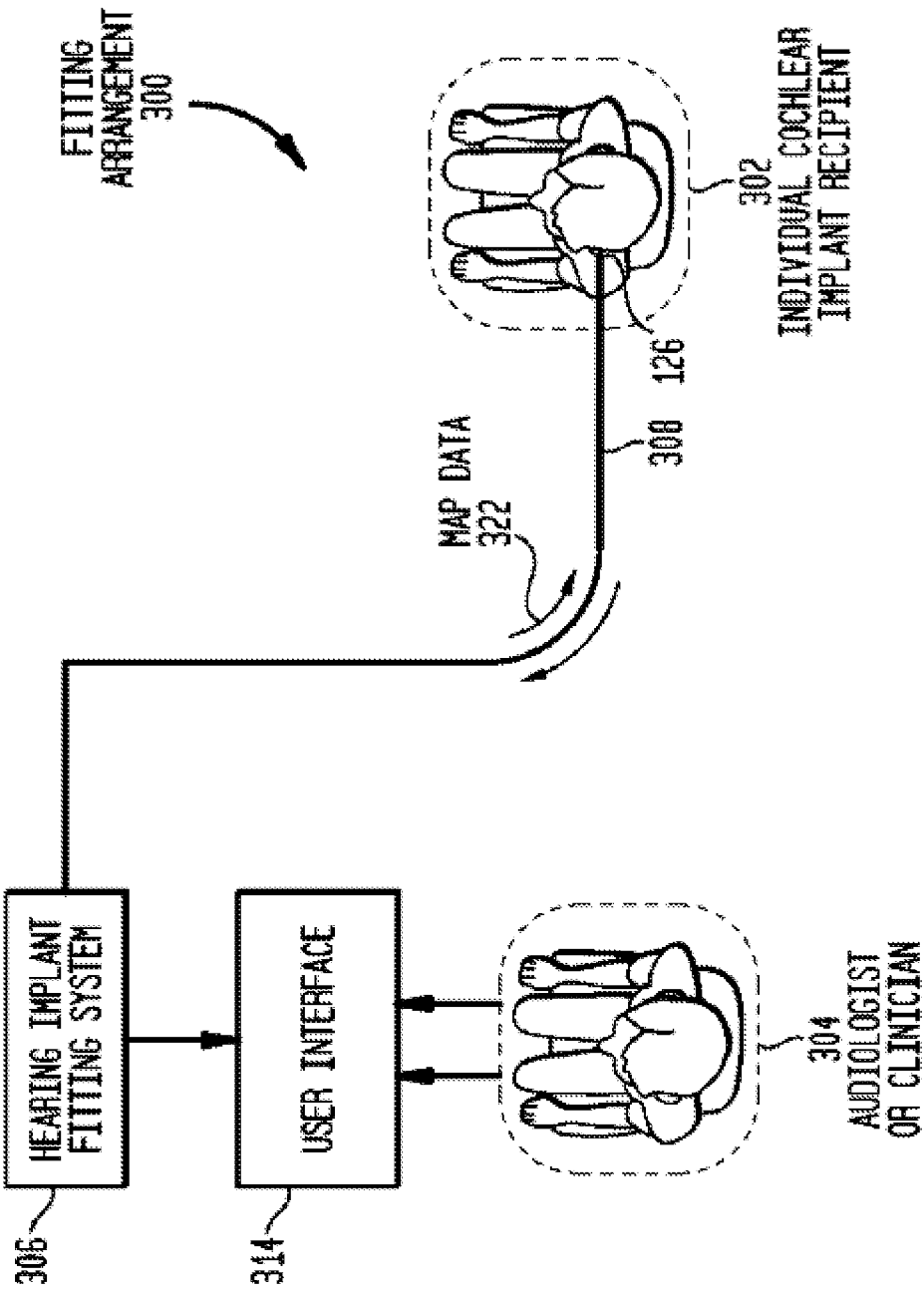
FIG. 3 presents an exemplary device in use according to an exemplary embodiment.

FIG. 3 is a schematic diagram illustrating one exemplary arrangement 300 in which a hearing implant fitting system 306 may be used to fit a cochlear implant that has been configured with complex stimulation channel electrode weights, in accordance with an embodiment. As shown in FIG. 3, an audiologist or clinician 304 may use a hearing implant fitting system 306 ("fitting system" herein) comprising interactive software and computer hardware to create individualized recipient map data 322 that are digitally stored on system 306 and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by a data communication link 308 with sound processing unit 126. It should be appreciated that although sound processing unit 126 and fitting system 306 are connected via a cable in FIG. 3, any communications link now or later developed may be utilized to communicably couple the implant and fitting system.

More specifically, in an exemplary embodiment, subsequent implantation of the cochlear implant 100 into the recipient and subsequent to setting (or at least assigning and adjusting) utilitarian weights of the respective complex stimulation channels, the cochlear implant 100 is fitted or customized to conform to the specific recipient desires. This procedure entails collecting information and determine patient specific parameters such as threshold levels (T levels) and maximum comfort levels (C levels) for one or more or all stimulation channels of the cochlear implant 100 developed according to the exemplary method(s) detailed above or by other methods, which, in at least some instances results in residual interactions between neighboring electrode channels. That is, the following fitting methods can be applied to an implanted cochlear implant 100 utilizing focused multipolar stimulation where simultaneous channel interactions occur for neighboring electrode channels (i.e., electrode channels that are immediately adjacent to one another/there are no electrodes in between the interacting electrode channels). It is noted that in an exemplar embodiment, all channels detailed herein are multipolar stimulation channels. That said, in some embodiments, not all of the channels are multipolar stimulation channels. Accordingly, some embodiments include one or more or all channels being multipolar stimulation channels (i.e., in a cochlear implant having 22 channels, 1, 2, 3, 4, 5, 6, 7, 8, 9, 10, 11, 12, 13, 14, 15, 16, 17, 18, 19, 20, 21 or all 22 channels can be multipolar stimulation channels).

Figure 4:
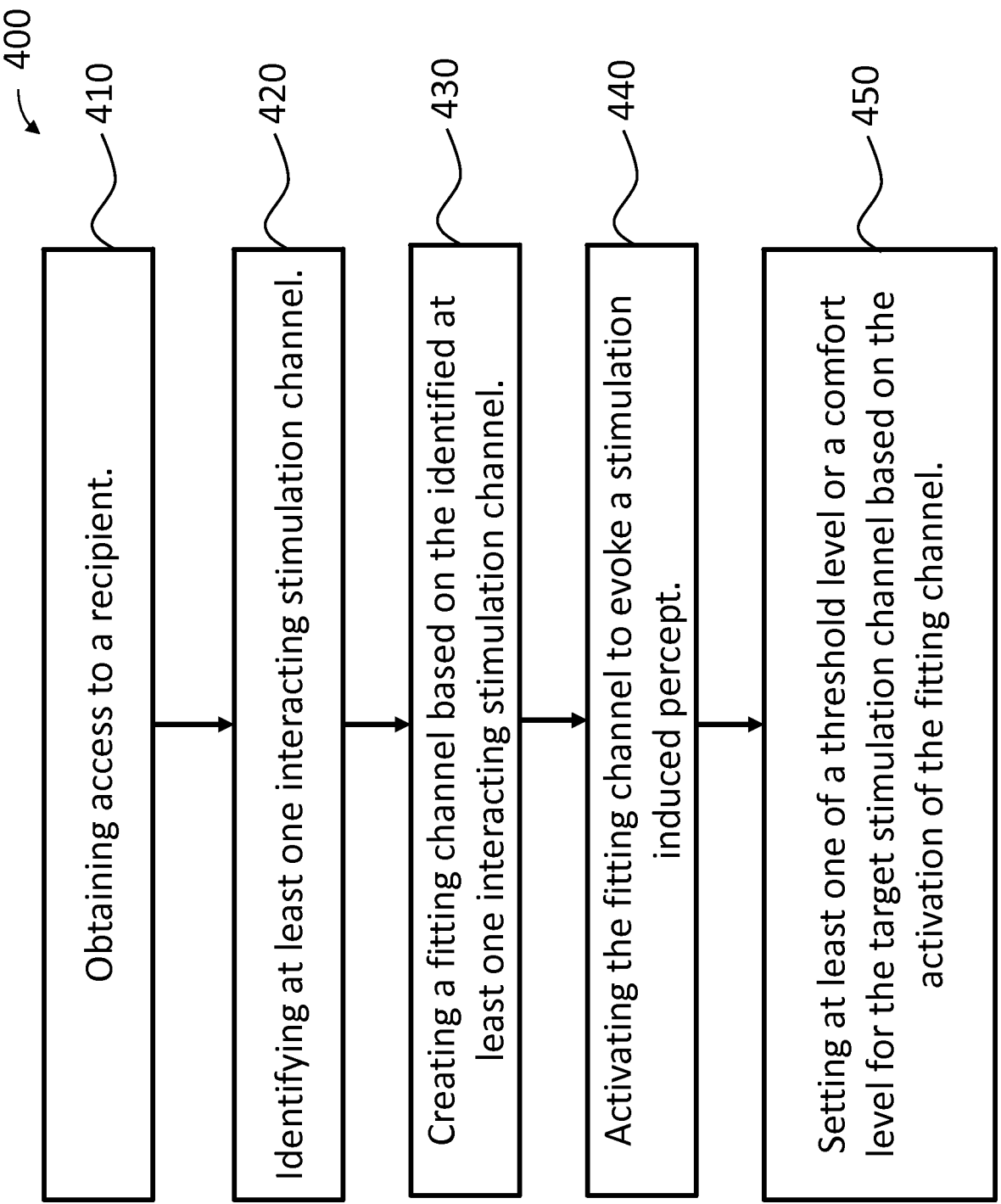
FIG. 4 presents an exemplary flowchart for an exemplary algorithms according to an exemplary embodiment.

Referring now to FIG. 4, there is an exemplary flowchart 400 for a method including method actions 410-450. Method action 410 entails obtaining access to a recipient having a plurality of electrodes of an electrical stimulating device implanted in the recipient. In an exemplary embodiment, the recipient can correspond to a recipient having the anatomical structure present in FIG. 1 above who also has the cochlear implant 100 implanted therein, where the cochlear implant 100 is configured to apply electrical stimulation to the recipient via the plurality of electrodes by activating a plurality of stimulation channels. In an exemplary embodiment, an audiologist or the like executes method action 410 using the arrangement of FIG. 3. It is noted that method action 410 can be performed in-person (e.g., the audiologist and the recipient are at the same location) or, in other embodiments, can be performed remotely (e.g., the audiologist is remote from the recipient, the audiologist obtaining access to the recipient via, for example, an internet or phone link, etc.).

Method action 420 entails identifying at least one interacting stimulation channel of the plurality of stimulation channels that interacts with a target stimulation channel of the plurality of stimulation channels during autonomous operation of the cochlear implant (i.e., operation of the cochlear implant during normal operation to evoke a hearing percept/operation of the cochlear implant after the fitting process). In an exemplary embodiment, the action of identifying at least one interacting stimulation channel includes identifying all interacting stimulation channels that at least substantially interact with the target stimulation channel during autonomous operation of the stimulating device.

By "target stimulation channel," it is meant the stimulation channel that corresponds to a given frequency and/or given range of frequencies, where the channel is based on an electrode (a base electrode) of the electrode array 146 of the cochlear implant 100 that is located in the tonotopically mapped cochlea at the location corresponding to that frequency/range of frequencies.

By way of example only and not by way of limitation, for purposes of further illustration, with reference to FIG. 2, the target stimulation channel can be the channel based on electrode 5 of the electrode array 146 (it can be a channel based on another electrode other than electrode 5, but for the purposes of the present discussion, the channel based on electrode 5 will be utilized). It is noted that in at least some embodiments, method 400 will be executed for a plurality of channels. By way of example only and not by way of limitation, all channels of the cochlear implant 100, and thus, by way of example only and not by way of limitation there will be 22 target stimulation channels based respectively on electrodes 1-22 of electrode array 146 of FIG. 2.

By "interacting stimulation channel that interacts with the target stimulation channel," it is meant a stimulation channel that interacts with the target stimulation channel at least at supra threshold levels when the interacting stimulation channel is activated at the same time as the target stimulation channel. By way of example only and not by way of limitation, in cochlear implants utilizing multipolar focusing corresponding to the teachings of the '301 publication, where simultaneous channel interactions are eliminated for stimulation channels more than one electrode apart (e.g., with reference to the just-detailed exemplary scenario where the base electrode is electrode 5, stimulation channels respectively corresponding to channels based on base electrodes 1-3 and 7-22), the interacting stimulation channels can correspond to stimulation channels based on electrode 4 and electrode 6 (with continuing reference to FIG. 2). Thus, with respect to this conceptual example, all interacting stimulation channels that at least substantially interact with the target stimulation channel that is based on electrode 5 during autonomous operation of the cochlear implant correspond to the channels that are based on electrodes 4 and 6, respectively. That said, it is noted that in embodiments where the current spread from the electrode array is such that there are more than three channels that interact with one another (e.g., such as utilizing implementations that do not embrace the teachings of the aforementioned '301 publication), the teachings detailed herein can be applied to such embodiments. Thus, there may be more than two interacting channels that interact with the target channel.

It is noted that in some instances, where the target stimulation channel is based on one of the electrodes at the proximal or distal ends of the electrode array 146 (e.g. electrode 1 and electrode 22, respectively), in embodiments utilizing multipolar focusing corresponding to the teachings of the '301 publication, there may be only one interacting stimulation channel because there are no electrodes proximal or distal, respectively, to those electrodes. That is, in an exemplary embodiment, the target stimulation channel based on electrode 1 may only have one interacting stimulation channel; that stimulation channel being based on electrode 2. Further, in an exemplary embodiment, the target stimulation channel based on electrode 22 may only have one interacting stimulation channel, that stimulation channel being based on electrode 21.

After method action 420 is executed, method action 430 is executed, which entails creating a fitting channel based on the identified at least one interacting stimulation channel and the target stimulation channel. In an exemplary embodiment, the fitting channel is a hybrid channel that, in at least some embodiments, is not utilized during autonomous operation of the cochlear implant 100. (That is, in an exemplary embodiment, there is a method of utilizing a cochlear implant 100 which was fit into a recipient utilizing a fitting channel, but where during use of the cochlear implant to evoke a hearing percept during autonomous use of the cochlear implant, the fitting channel is not utilized. Instead, the normal stimulation channels are utilized/the stimulation channels utilized to develop the fitting channel(s) is utilized.) The development of the fitting channel and various features of the fitting channel will be further detailed below.

After method action 430 is executed, method action 440 is executed, which entails activating the fitting channel created in method action 430. In an exemplary embodiment, the activation of the fitting channel evokes a stimulation induced percept, which, in embodiments where method 400 is executed for a cochlear implant 100, corresponds to a stimulation induced hearing percept (in embodiments where the electrical stimulation device is, for example, an retinal stimulation device, the percept would be a visual percept, etc.).

Method action 400 further includes method action 450, which entails setting at least one of a threshold level or a comfort level for the target stimulation channel based on the activation of the fitting channel as activated in method action 440. Thus, in an exemplary embodiment, during normal autonomous operation of the cochlear implant 100, the threshold level and/or comfort level of a given channel is developed based on a stimulation regime that is different from the stimulation regime that results from activation of that channel. Additional details of this method action will be described below.

With respect to method action 420, the action of creating the fitting channel can correspond to merging the identified at least one interacting stimulation channel with the target stimulation channel.

In an exemplary embodiment of method action 420, the stimulation channels have respective weights for respective electrodes of the plurality of electrodes, and the action of creating the fitting channel includes summing respective electrode weights for the at least one interacting stimulation channel and respective electrode weights for the target stimulation channel. In at least some embodiments, the weights correspond to weights of respective currents (whether positive (source currents) or negative (sink currents)) of respective electrodes for each channel. By way of example only and not by way of limitation, for purposes of illustrating the concept: weighting of the target stimulation channel based on electrode number 5 corresponds to 1.0 for electrode 5, and −0.25 and −0.25 for electrode numbers 4 and 6, and −0.026 for the remaining electrodes; weighting for the interacting stimulation channel based on electrode number 4 is 1.0 for electrode 4, and −0.25 and −0.25 for electrode numbers 3 and 5, and −0.026 for the remaining electrodes; and weighting for the interacting stimulation channel based on electrode number 6 is 1.0 for electrode 6, and −0.25 and −0.25 for electrode numbers 5 and 7, and −0.026 for the remaining electrodes. Accordingly, in this exemplary illustrative conceptual scenario, where the fitting channel is created by summing respective electrode weights, an exemplary fitting channel can have a weighting of 0.5 for electrode number 5, 0.724 for electrode numbers 4 and 6, −0.302 for electrode numbers 3 and 7, and −0.078 for the remainder electrodes. Accordingly, the merged channel for a target channel based on electrode number 5 is a combination of the channels 4, 5 and 6 which are respectively based on electrodes 4, 5 and 6. In such an exemplary embodiment, channel 4 and 6 are the only two channels that at least substantially interact with target channel 5. In an alternative embodiment, if more channels than channels 4 and 6 interact with target channel 5, the merged channel for the target channel 5 may include additional channels (e.g. channels 3 and 7 that are based on electrodes 3 and 7, respectively).

Thus, in an exemplary embodiment, there is a method action that entails combining all channels that interact with the target channel together with the target channel to create a merged channel that is made up of the summed electrode weights of some and/or all of the interacting channels.

It is noted that in some alternate embodiments, the fitting channel can be created by other methods than summing the respective electrode weights. Any method that will enable the teachings detailed herein and/or variations thereof to be practiced can be utilized in at least some embodiments.

Figure 5:
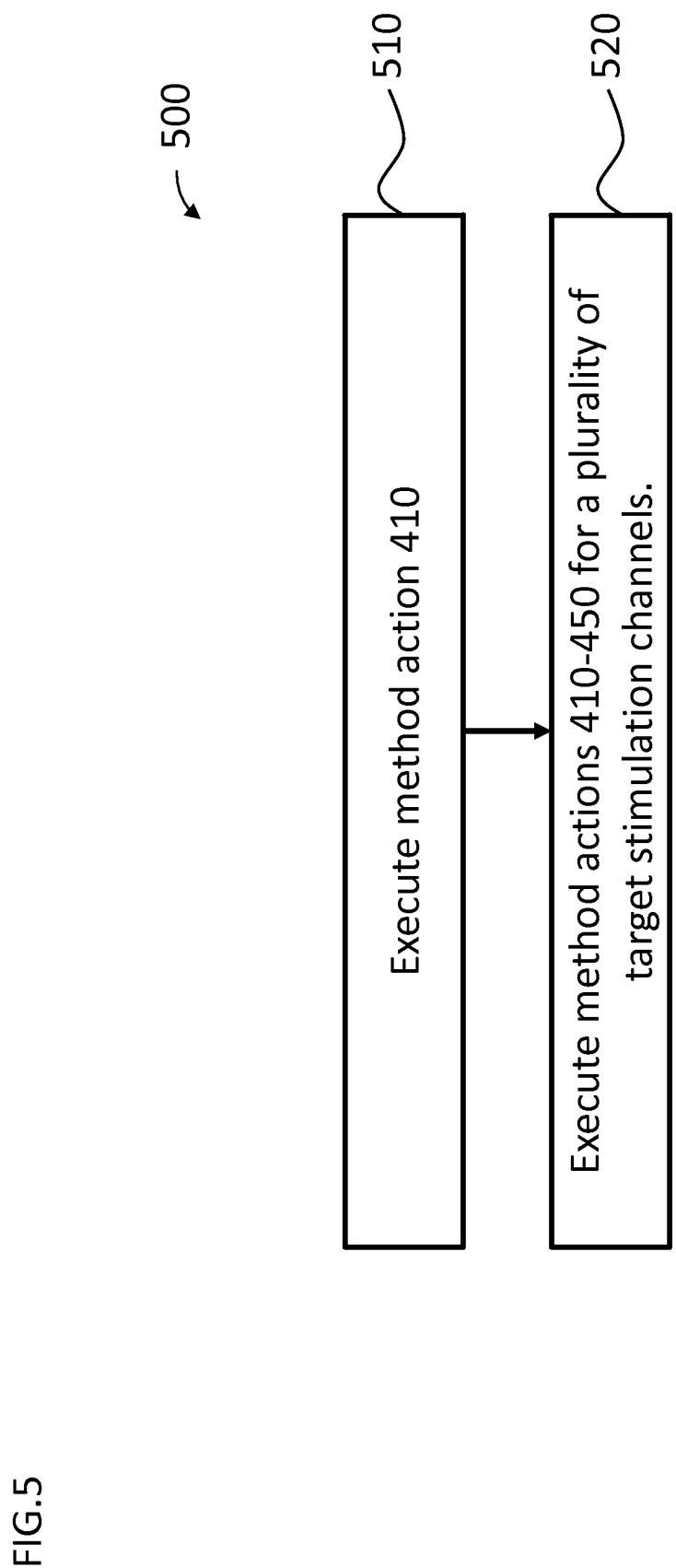
FIG. 5 presents another exemplary flowchart for an exemplary algorithms according to an exemplary embodiment.

FIG. 5 details a flow chart for another exemplary method 500, which includes method actions 510 and 520. Specifically, method action 510 entails executing method action 410 as detailed above. Method action 520 entails executing method actions 420 to 450 for two or more target stimulation channels. In an exemplary embodiment, method action 520 entails executing method actions 420 to 450 for every target stimulation channel of the cochlear implant (e.g., for each of the 22 stimulation channels respectively based on each of the 22 electrodes), or at least every target stimulation channel of the cochlear implant that is desired to be measured.

In an exemplary embodiment, this is done serially, one stimulation channel at a time. In an exemplary embodiment, the method starts with electrode channel 1 based on electrode 1, and then proceeds to electrode channel 2 based on electrode 2, and proceeds accordingly to electrode channel 22, which is based on electrode 22. In an alternative embodiment, the method starts with electrode channel 22 based on electrode 22, and then proceeds to electrode channel 21 based on electrode 21, and proceeds accordingly to electrode channel 1, which is based on electrode 1. In yet another alternative embodiment, the method starts with electrode channel 1 based on electrode 1, and then proceeds to electrode channel 11 based on electrode 11, and proceeds to electrode channel 22, which is based on electrode 22, and then proceeds to another channel, etc.

In an exemplary embodiment, the order in which the target stimulation channels are addressed can be any order that can have utilitarian value. The order can be random (e.g. based on a random selection by a computer or the like). In an exemplary embodiment, not all electrode channels are addressed. Any order and/or any selection of electrode channels that can enable the teachings detailed herein and/or variations thereof to be practiced can utilize in at least some embodiments.

Still with respect to method action 520, in an exemplary embodiment, methods 410-450 are executed for a first target channel (e.g., target channel 5 based on electrode 5 as detailed above), and the respective interacting stimulation channels are respective first interacting stimulation channels (that include one or more channels—channels 4 and 6 in the above example), to develop/create a first fitting channel for stimulation channel 5. (It is noted that the numerical identifiers used herein, such as the term "first" as just used and "second" as will soon be used, connote features of the teachings detailed herein that are related to corresponding numerically identified features, at least for specific embodiments. It is a naming convention and does not have a temporal or primacy meaning.) In this exemplary embodiment, methods 410-450 are executed for a second target channel (e.g., target channel 6 based on electrode 6) and the respective interacting stimulation channels (e.g., channels 5 and 7 based on electrodes 5 and 7, respectively) are respective second interacting stimulation channels (that include one or more channels), to develop/create a second fitting channel for stimulation channel 6 based on the identified second interacting stimulation channel(s) and the second target stimulation channel. The method thus further includes activating the second fitting channel to evoke a stimulation induced percept (e.g., a hearing percept), and setting at least one of a threshold level or a comfort level for the second target stimulation channel based on activation of the second fitting channel.

As can be seen from the above, in this exemplary embodiment, one of the first interacting stimulation channel(s) is the second target channel (channel 6), and one of the second interacting stimulation channels is the first target channel (channel 5). In an exemplary embodiment, this is because the first target channel and the second target channel are neighbors of each other (i.e., they are immediately adjacent to one another relative to other electrodes of the stimulating device). In an alternate embodiment, where the first target channel is not a neighbor of the second target channel, and where the focused stimulation of the '301 publication is utilized such that the only channels that interact with the target channel are the channels based on electrodes that are neighbors of the electrode upon which the target channel was based, none of the first interacting stimulation channels would be the second target channel, and none of the second interacting stimulation channels would be the first target channel. That said, in an exemplary embodiment where the first target channel and the second target channel were separated from each other only by one channel (i.e., the electrodes upon which the respective channels are based are separated from each other only by one electrode), one of the first interacting stimulation channels is one of the second interacting stimulation channels.)

Still with respect to this exemplary embodiment, method actions 410-450 are executed for additional target channels. With respect to the embodiment where the cochlear implant 100 includes 22 channels based on 22 electrodes, method actions 410-450 are executed for a third target channel, a fourth target channel, a fifth target channel, and so on up to twenty-two target channels (or fewer if not all channels are to be addressed in a given method).

Accordingly, in an exemplary embodiment, method actions 410-450 are executed for a third target channel, where the third target channel is based on an electrode that is different from an electrode upon which the first and second target channels are based (e.g., with respect to the presently described embodiment, where the first target channel is based on electrode 5 and the second target channel is based on electrode 6, the third target channel can be based on electrode 1, electrode 2, electrode 3, electrode 4, electrode 7, electrode 8, etc.). Method actions 410-450 are executed for this third target channel to develop/create a respective third fitting channel based on identified third interacting stimulation channels that interact with the third target stimulation channel. In an exemplary embodiment, after development thereof, the third fitting channel is activated to evoke a stimulation induced percept, and at least one of a threshold level or a comfort level is set for the third target stimulation channel based on activation of the third fitting channel.

By way of example only and not by way of limitation, for purposes of demonstrating that some target channels only have one other interacting channel, at least when practicing the teachings detailed herein with the stimulation regimes of the '301 patent, the third target channel is channel 1, which is based on electrode 1, and the respective interacting stimulation channel(s) (e.g., channel 2 based on electrode 2) are, for the purposes of classification, respective third interacting stimulation channel(s). In the exemplary embodiment where the target channel is channel 1 based on electrode 1, the third interacting stimulation channel(s) only include one channel, channel 2 based on electrode 2, because the target channel is based on the most proximal electrode, electrode 1. Conversely, if the third target channel was a channel based on electrode 2, the third interacting stimulation channels would include two channels: channel 1 based on electrode 1 and channel 3 based on electrode 3, at least when utilizing the teachings of the '301 publication.

Method action 520 continues along this trajectory for the various target channels of interests, whether it be for some of the target channels of the cochlear implant 100 or all of the target channels of the cochlear implant 100, where the order of addressing the target channels presented herein is exemplary and provided for illustrative purposes.

It is noted that in at least some embodiments, such as the example just detailed where the third target channel is based on electrode 1 or based on electrode 2, none of the third interacting stimulation channel(s) substantially interact with the first target stimulation channel (or the second target stimulation channel) during autonomous operation of the cochlear implant using stimulation according to the teachings of the '301 publication (e.g., none of the channels that make up the third interacting stimulation channels are channels that are in the second interacting stimulation channels, which comprise channels 5 and 7 based on electrodes 5 and 7, respectively, or are channels that are in the first interacting stimulation channels, which comprise channels 4 and 6 based on electrodes 4 and 6, respectively, as noted above). That said, if the third target channel was based on electrode number 3 or number 4, one of the third interacting stimulation channels would substantially interact with the first target stimulation channel (the channel based on electrode number 5) during autonomous operation of the cochlear implant (if the target channel is based on electrode 3, a channel based on electrode 4 would interact with the first target stimulation channel and the third target stimulation channel, if the target channel was based on electrode number 4, an interacting channel with the target channel would be the first target channel).

That said, in an alternate embodiment that does not utilize the stimulation strategies of the '301 publication, there may be more than one or two channels that interact with the target channel. That is, the teachings of the '301 publication are directed towards limiting channel interaction as much as possible, and this typically results in only interaction with channels that are based on electrodes that are neighbors of the electrode upon which the target channel is based. Conversely, the teachings detailed herein and/or variations thereof can be practiced utilizing stimulation strategies different from the '301 publication. Accordingly, in an exemplary embodiment, channel interaction is not limited to only interaction with the channels that are based on electrodes that our neighbors of the electrode upon which the target channel was based. By way of example only and not by way of limitation, for a target channel based on electrode 15, channels respectively based on electrodes 13, 14, 16 and 17 can interact with target channel 15. Accordingly, in an exemplary embodiment, the hybrid fitting channel can be a merged channel corresponding to channels based on electrodes 13-17 (five electrodes).

Figure 6:
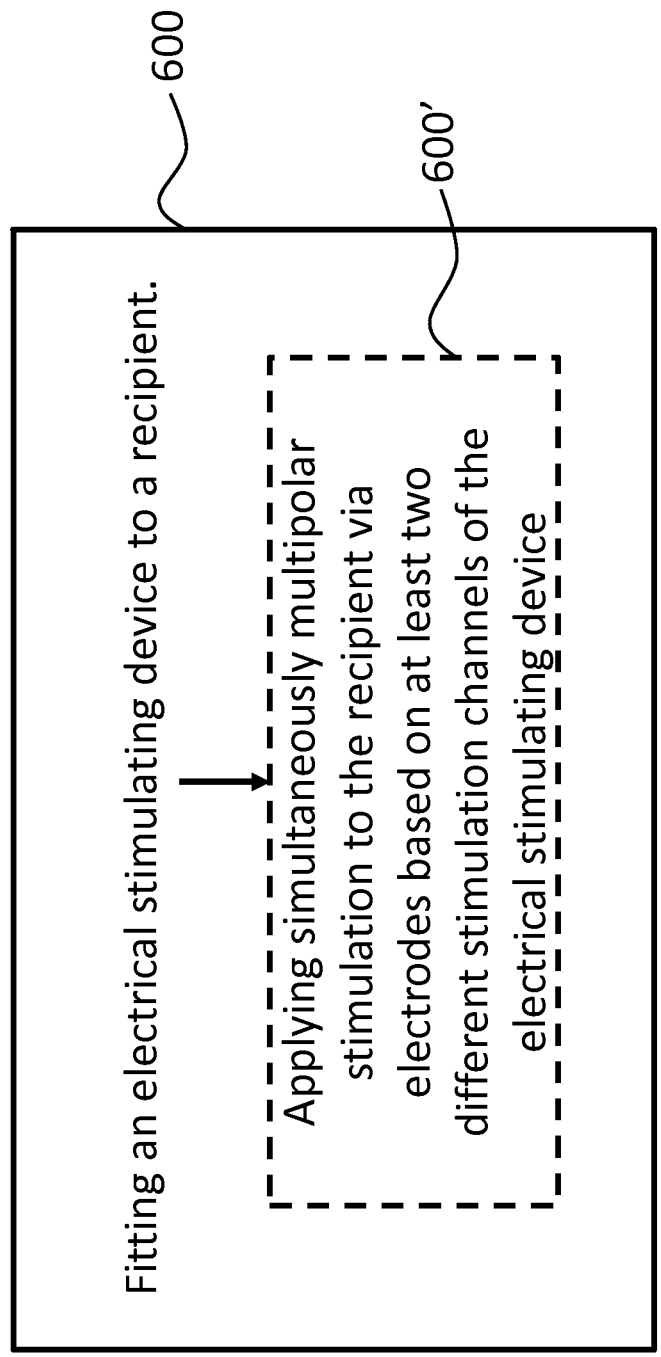
FIG. 6 presents another exemplary flowchart for an exemplary algorithms according to an exemplary embodiment.

Now with reference to FIG. 6, there is an exemplary method 600 which entails fitting an electrical stimulating device (e.g., a cochlear implant) to the recipient where the electrical stimulating device includes electrodes implanted in the recipient and where the electrical stimulating device is a multipolar electrical stimulating device. In an exemplary embodiment, the electrical stimulating device is a cochlear implant that operates according to the teachings of the '301 publication. Method 600 includes a sub-action 600', which entails the simultaneous application of multipolar channels to the recipient via the electrodes based on at least two different stimulation channels of the electrical stimulating device. In an exemplary embodiment, sub-action 600' entails stimulating the recipient using a fitting channel referenced above, which is based on at least two different stimulation channels (and, in at least some instances with respect to electrodes 2-21 of an electrode array having 22 electrodes, at least three different stimulation channels).

In an exemplary embodiment, method 600 further includes determining a threshold level specific to the recipient based on the simultaneously applied multipolar channels. Alternatively and/or in addition to this, in an exemplary embodiment, method 600 further includes determining a comfort level specific to the recipient based on the simultaneously applied multipolar channels.

In an exemplary embodiment, the determination of the threshold level and/or comfort level can be used as a basis upon which to execute method action 450 detailed above.

The threshold level and/or the comfort level can be determined utilizing any method that can enable the teachings detailed herein and/or variations thereof to be practiced. For example, objective and/or subjective methods for determining threshold levels and/or comfort levels can be utilized. In an exemplary embodiment, utilizing the simultaneously applied multipolar channels based on at least two different stimulation channels can be utilitarian in that by combining some and/or all channels that interact with the target channel together with the target channel into a fitting channel, and using that fitting channel to apply the simultaneous multipolar channels, threshold levels and/or comfort levels that more accurately reflect the intensity of the hearing percept that occurs when channels interact can be identified. That is, in contrast to applying multipolar stimulation of the recipient utilizing only a single stimulation channel to identify threshold levels and/or comfort levels, the teachings detailed herein and or variations thereof can enable the determination of threshold levels and/or comfort levels that take into account channel interactions that may be seen during normal operation use/autonomous use of the cochlear implant.

Figure 7:
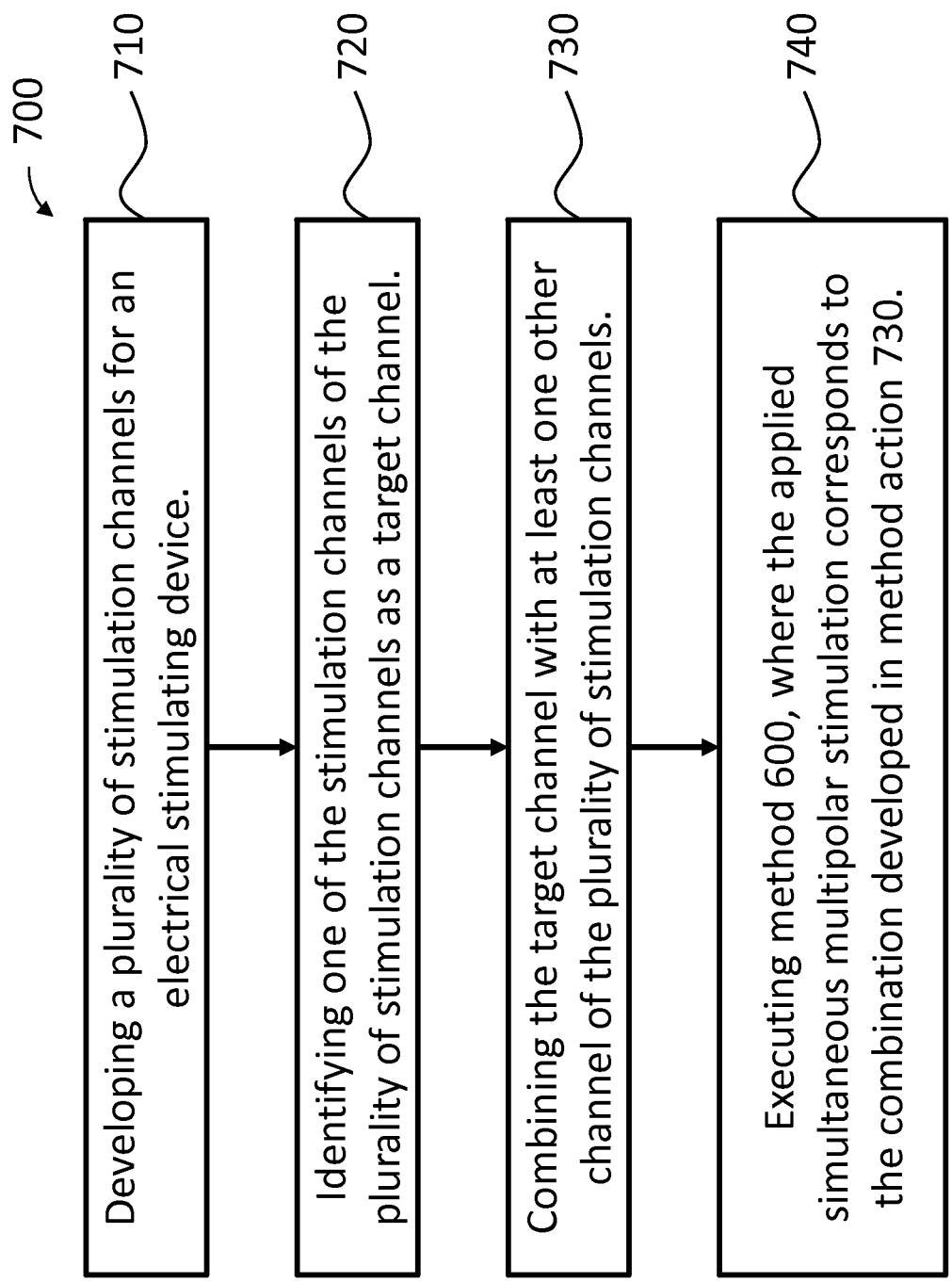
FIG. 7 presents another exemplary flowchart for an exemplary algorithms according to an exemplary embodiment.

FIG. 7 provides an exemplary method 700 according to an exemplary embodiment that includes method 600 as will now be detailed.

Method 700 includes method action 710, which entails developing a plurality of stimulation channels for an electrical stimulating device, such as the cochlear implant 100 detailed above. In an exemplary embodiment, the development of the stimulation channels of method action 710 is executed according to some and/or all of teachings of the '301 publication. It is noted that in alternative embodiments, other methods of developing stimulation channels can be utilized. By way of example only and not by way of limitation, the development of stimulation channels of method action 710 is executed according to some and/or all of the teachings of U.S. Pat. No. 7,780,573. Any device, system, and/or method that can enable the development of stimulation channels can be utilized in at least some embodiments.

As noted above, in an exemplary cochlear implant 100, there are 22 stimulation channels. For purposes of conceptual illustration, however, method action 710 will be described in terms of two and three stimulation channels. Accordingly, in an exemplary embodiment, method action 710 entails developing at least a first stimulation channel and a second stimulation channel, or developing at least a first, second and third stimulation channel. (Note that these do not necessarily correspond to a respective channels respectively based on electrodes 1, 2 and 3. That is, the identifier "first" and "second," etc., are utilized herein as just that—identifiers.)

Method 700 further includes method action 720, which entails identifying as a target stimulation channel one of the stimulation channels of the plurality of stimulation channels developed in method action 710. By way of example only and not by way of limitation, the first and second stimulation channels correspond to stimulation channels based on, respectively, the first and second electrodes, and the first stimulation channel (channel 1) corresponds to the target channel. Still further by way of example only and not by way of limitation, the first and second stimulation channels developed in method action 710 can correspond to stimulation channels, based on, respectively, the fifth electrode and the sixth electrodes (channels 5 and 6, respectively), and in at least some embodiments, there is a third stimulation channel developed in method action 710 which can correspond to a channel based on the fourth electrode (channel 4). In this exemplary embodiment, the first stimulation channel developed in method action 710 can correspond to the channel based on the fifth electrode (channel 5), with the second and third stimulation channels correspond to the channel based on the fourth and sixth electrode (channels 4 and 6), respectively, and executing method action 720 results in the identification of the first channel as the target channel.

Method 700 further includes method action 730, which entails combining the target channel with at least one other channel of the plurality of stimulating channels developed in method action 710. In an exemplary embodiment, method action 730 results in the development of a merged channel. Method action 730 can be executed according to any of the teachings detailed herein or variations thereof (e.g., the teachings detailed above to develop a fitting channel) or any other method that will enable the teachings detailed herein to be executed.

After combining the target channel with at least one other channel, method 700 proceeds to method action 740, which entails executing method 600, where the applied simultaneous multipolar stimulation applied in method 600 corresponds to the combination developed in method action 730, and where the at least two different stimulation channels include at least the first stimulation channel and the second stimulation channel (and, in some instances, the third stimulation channel if applicable) developed in method action 710. In an exemplary embodiment, the applied simultaneous multipolar channels applied in method 600 corresponds to the merged channel developed in method action 730.

In at least some exemplary embodiments of the method 700, the channels combined in method action 730 with the target channel are channels that interact with the target channel (e.g., channels that interact when stimulation is applied by a cochlear implant according to the teachings of the '301 publication). In an exemplary embodiment, the channels that are combined with the target channel in method action 730 are limited to the channels that interact with the target channel. That is, no channel that does not interact with the target channel is combined with the target channel in method action 730. Thus, in an exemplary embodiment, the merged channel developed in method action 730 is a channel that does not include any other channels other than the first and second channel detailed above (or the first, second and third channel detailed above with respect to the alternate scenarios where two channels are combined with the target channel, both of the two channels interacting with the target channel). Indeed, along these lines, in at least some instances, method action 710 entails developing more channels than the number of channels that are combined in method action 730. Thus, referring to the scenario where three channels are combined in method action 730, in an exemplary embodiment of method 700, method action 710 entails developing the fourth stimulation channel, and the merged channels resulting from method action 730 do not include this fourth stimulation channel. Indeed, referring to an exemplary embodiment where method 700 is implemented with a cochlear implant having 22 channels, method action 710 entails developing 22 channels, where method action 730 entails only combining three of those 22 channels or only some other subset of those 22 channels.

Figure 8:
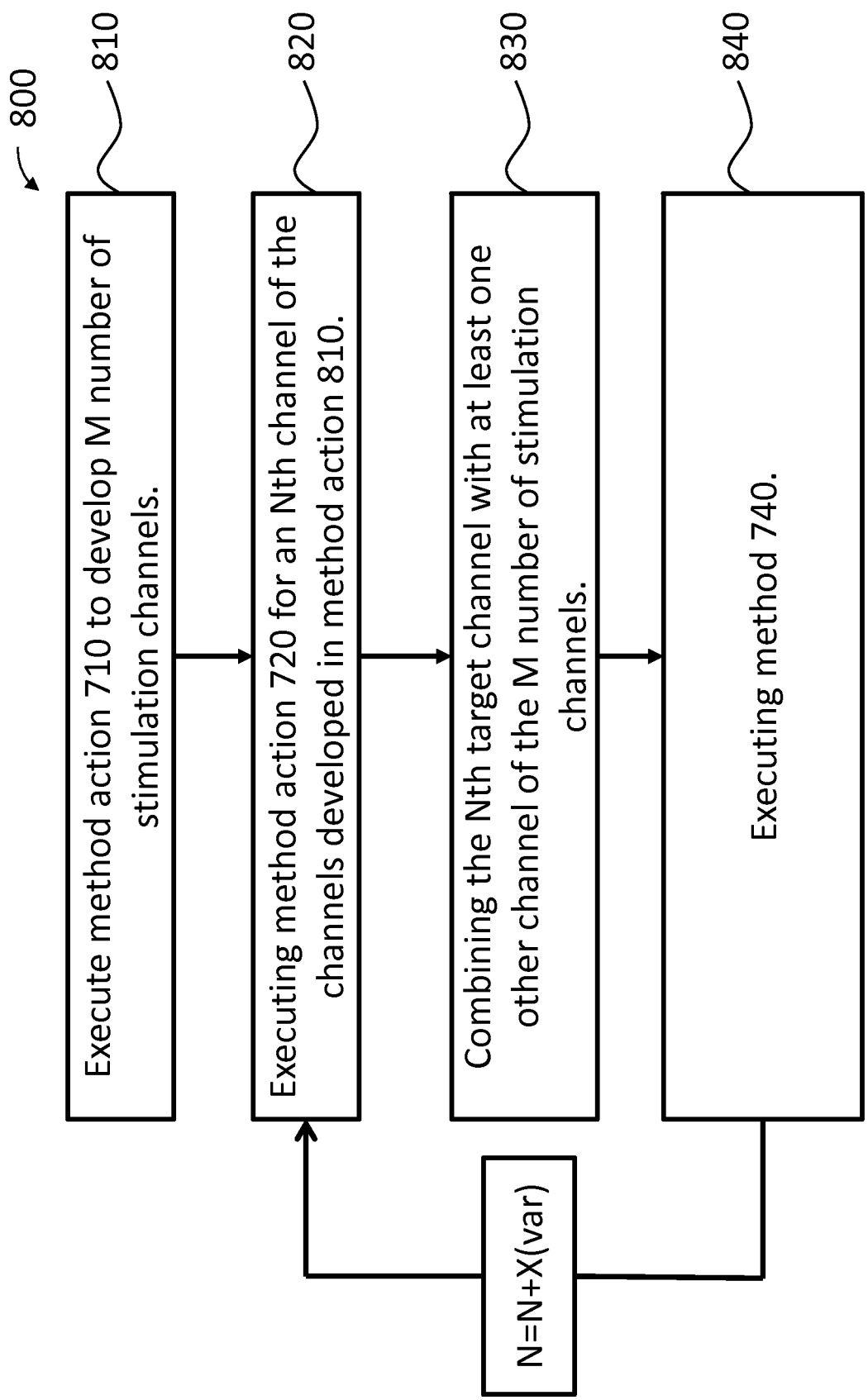
FIG. 8 presents another exemplary flowchart for an exemplary algorithms according to an exemplary embodiment.

In some embodiments, a number of the method actions of method 700 are repeated. For example, method action 730 may be repeated a number of times, such as 22 times; one time for each channel of the exemplary cochlear implant that has 22 channels. Accordingly, referring now to FIG. 8, there is an exemplary method 800 presented that includes method action 810 which entails executing method action 710 detailed above to develop M number of channels in an exemplary embodiment. In an embodiment where a stimulating device such as a cochlear implant has 22 channels, M can equal 22. Method 800 further includes method action 820, which entails executing method action 720 for an Nth channel of the M number of channels developed in method action 810. By way of example only and not by way of limitation, in an exemplary embodiment for a cochlear implant having 22 channels, the Nth channel is a channel based on the first electrode (although another channel based on another electrode can be used), and thus the target channel is a channel based on the first electrode (channel 1). Method 800 further includes method action 830, which entails combining the Nth target channel with at least one other channel of the M number of channels developed in method action 810. In an exemplary embodiment, method action 830 is executed according to method action 730 detailed above. Thus, in an exemplary embodiment, method action 830 entails combining the Nth target channel with one or two other channels, as only one or two other channels interact with the target channel. In an exemplary embodiment where the Nth target channel is based on electrode 1 (channel 1), method action 830 can entail combining that channel with only the channel based on electrode 2 (channel 2), as that is the only channel that interacts with the channel based on electrode 1. In an exemplary embodiment where the Nth target channel is based on electrode and 2, method action 830 can entail combining that channel with only the channel based on electrode 1 and the channel based on electrode 3, as those are the only two channels that interact with the channel based on electrode 2.

Method 800 further includes method action 840, which entails executing method action 740 detailed above using the combined channel obtained in method action 830. After method action 740 is executed, method 800 returns to method action 820, which entails executing method action 720 for the Nth channel of the channels developed in method action 810, where N=N+X(var), where X(var)=1, and thus if the Nth channel was the channel based on electrode 1 the last time method action 820 was executed, the Nth channel is the channel based on electrode 2 this time that method action 820 is executed. Method 800 proceeds accordingly through method actions 830 and 840, and then back to method action 820, until, for example, N=M, at least where X=1. Accordingly, method actions 820, 830, and 840 are executed for all of the channels of interest. In the exemplary embodiment just detailed, if there are 22 channels of interest/22 channels developed (M=22), method actions 820, 830, 840, are executed 22 times if X(var) equals 1. That said, in an alternate embodiment, X(var) can be a different number (e.g. two, three, four, etc.), Consistent with the annotation of "var." Such an exemplary embodiment, method action 800 which entails skipping method actions 820, 830, and 840 for some channels. Note further that acts need not be a constant number throughout the execution of method 800. By way of example only and not by way of limitation, X(var) can vary from one iteration to another (e.g., the first time, X(var) equals 1, the second time, X equals 3, the third time X equals 2, the fourth, fifth and sixth time, X equals 1, etc.). That is, in embodiments where method actions 820, 830, and 840 are skipped for some channels, the skipping of channels need not be of a uniform pattern. That is, method actions 820, 830, and 840 are executed for the channels they are desired by the audiologist and/or that are deemed utilitarian, and other channels are skipped if it is determined that there is less utilitarian value (including no utilitarian value) in executing method actions 820, 830 and 8404 certain channels.

Also, note that X(var) can be a negative number in some instances.

Note further that in at least some embodiments, method 800 does not start with the first electrode along the electrode array of the cochlear implant 100. In an exemplary embodiment, method 800 starts with the most distal electrode (electrode 22) and proceeds "backwards" towards the most proximal electrode (electrode 1). Still further, in an exemplary embodiment, method action 800 starts with an electrode in between the most distal and most proximal electrodes.

Any order with respect to the electrodes that can enable the teachings detailed herein to be practiced can utilize in at least some embodiments.

In an alternative embodiment, method action 800 is executed such that method actions 820, 830 and 840 are executed for only some of the channels, where the channels for which these actions are executed are based on electrodes that are clustered at one portion of the cochlear array. By way of example only and not by way of limitation, this can entail executing method actions 820, 830 and 840 channels based on electrodes that correspond to specific frequencies/specific frequency ranges of the tonitopically mapped cochlea. For example, if it is determined that interaction of channels based on electrodes that correspond to high frequencies occurs more often and/or occurs with a greater deleterious effect than interaction of channels based on electrodes that correspond to other frequencies (e.g., medium frequencies and/or low frequencies), method actions 820, 830 and 840 can be executed only for the higher frequency channels. Alternatively, it is determined that interaction channels based on electrodes that correspond to low frequencies occurs more often and/or occurs with greater deleterious effect than interaction of channels based on electrodes that corresponds to other frequencies (e.g. medium and/or high frequencies), method actions 820, 830 and 840 can be executed only for the lower frequency channels, and so on.

Method actions 820, 830 and 840 can be executed, in at least some embodiments, for any channel and/or subset of channels of the electrical stimulating device.

Figure 9:
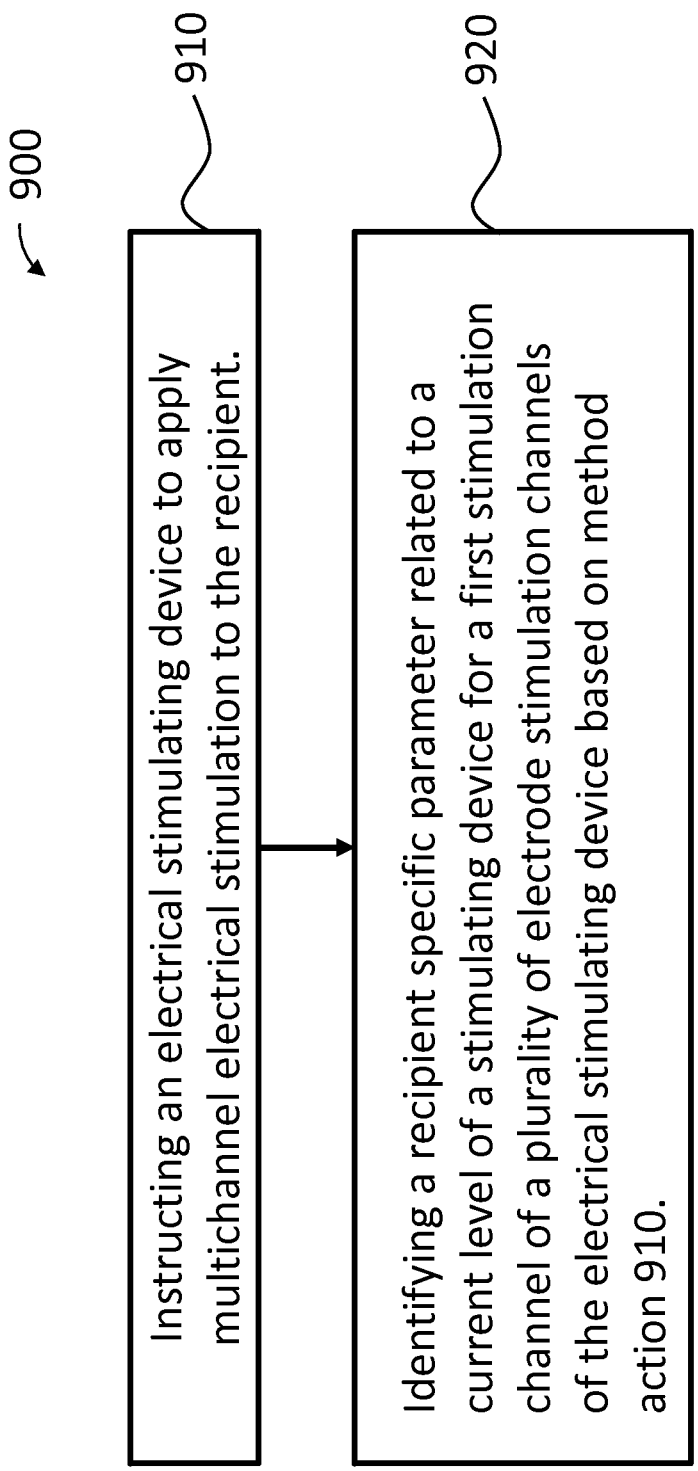
FIG. 9 presents another exemplary flowchart for an exemplary algorithms according to an exemplary embodiment.

FIG. 9 depicts a flowchart for a method 900 that corresponds to another exemplary algorithm according to an exemplary embodiment. Method 900 will be described in terms of a non-transitory computer readable medium, such as a computer program. However, it is noted that the method 900 can be practiced in another form (e.g. as a regular method). It is further noted that in at least some embodiments, any method detailed herein can be practiced in the form of a non-transitory computer readable medium comprising a computer programming having code to execute one or more or all of the method actions detailed herein. Indeed, it is noted that any method detailed herein corresponds to a disclosure for a device and/or system configured to execute that method. Further, it is noted that any device and/or system detailed herein corresponds to a disclosure for a method corresponding to the functionality of that device and/or system (not only just a method of utilizing the device and/or system, but the method executed by that device and/or system).

Accordingly, in an exemplary embodiment, there is a non-transitory computer readable medium having recorded thereon, a computer program for executing at least a portion of a method of fitting an electrical stimulating device including electrodes implanted in a recipient (e.g., such as the cochlear implant 100 of FIG. 1). The electrical stimulating devices configured to apply electrical stimulation to the recipient via the plurality of electrodes. In an exemplary embodiment, this computer program includes a code for executing method 900.

It is noted that while the teachings detailed herein are described in terms of an electrical stimulating device in the form of a cochlear implant, it is noted that in alternate embodiments are applicable to other types of stimulating devices. By way of example only and not by way of limitation, the teachings detailed herein and/or variations thereof can be applicable to a retinal prosthesis. Indeed, while the teachings detailed herein are generally directed towards a one-dimensional electrode layout (e.g. a cochlear electrode array), alternate embodiments can be applied to a two-dimensional electrode layout (e.g. such as the aforementioned retinal prosthesis). Further, in at least some embodiments, the teachings detailed herein can be directed towards a three-dimensional electrode layout. Accordingly, in an exemplary embodiment, the electrical stimulating device according the teachings detailed herein can be any type of electrical stimulating device which the present teachings can have utility when applied thereto.

As can be seen, method 900 includes method actions 910 and 920. Method action 910 entails instructing the electrical stimulating device to apply multichannel electrical stimulation to the recipient. Method action 920 entails identifying a recipient specific parameter related to a current level of a stimulating device for a first stimulation channel of a plurality of electrodes stimulation channels of the electrical stimulating device based on method action 910. By way of example only and not by way of limitation, the recipient parameter of the present embodiment can be a threshold level or a comfort level.

By "multichannel stimulation," it is meant a regime where parameters of the individual channels are adjusted such that the multichannel stimulation results in one or more or all of the electrodes providing stimulation at different current levels from that which would be the case if one of the individual channels was used for stimulation/the individual channels were activated separately. By way of example only and not by way of limitation, the multichannel stimulation can correspond to the merged channels detailed herein and/or to a fitting channel detailed herein, etc.

In an exemplary embodiment of the method 900, the multichannel stimulation is based on a first stimulation channel and a second stimulation channel and, optionally, a third stimulation channel and, optionally, additional channels. In an exemplary embodiment, these first, second and third stimulation channels can correspond to the exemplary stimulation channels detailed above. Accordingly, in an exemplary embodiment, the first stimulation channel corresponds to activation of a plurality of electrodes of the electrical stimulating device (some or all) at respective first weights, and the second stimulation channel corresponds to activation of a plurality of electrodes of the electrical stimulating device at respective second weights. With respect to the currently described exemplary embodiment, at least one of the weights of the first weights is different from a respective weight of the second weight. In an exemplary embodiment, two or more or all of the weights are different from respective weights of the second weights.

In an exemplary embodiment, the multichannel stimulation applied in method action 910 entails activating the plurality of electrodes of the electrical stimulating device at respective third weights (e.g., this can be a fitting channel). In accordance with the teachings above, at least one of the weights of the third weights is different from the respective weights of the first and second weights. In this regard, at least one of the weights of the third weights is respectively the summation of the respective first weights and the respective second weights.

Referring back to the non-transitory computer readable medium of the present embodiment, the medium can include code for identifying a second recipient specific parameter related to a second current level of the stimulating device for the first stimulation channel by instructing the stimulating device to apply the multichannel stimulation to the recipient. By way of example only and not by way of limitation, the first recipient parameter of the present embodiment can be a threshold level and the second recipient specific parameter can be a comfort level or, in an alternative embodiment vice versa.

As noted above, in an exemplary embodiment, the electrical stimulating device that is utilized to execute at least part of method 900 is a cochlear implant, such as cochlear implant 100 described above, and the electrodes are part of an electrode array of the cochlear implant. In an exemplary embodiment of this exemplary embodiment, the multichannel stimulation is based on at least three different stimulation channels respectively corresponding to different base electrodes of the stimulating device. Further, one of the three different stimulation channels is the first stimulation channel, and the first stimulation channel corresponds to a first base electrode. Also, at least two of the stimulation channels other than the first stimulation channel correspond to base electrodes immediately adjacent the first electrode on respective different sides of the first electrode relative to position along the electrode array.

In an exemplary embodiment of method 900, the multichannel stimulation is based on the first simulation channel and a second stimulation channel, the first stimulation channel corresponds to activation of a first electrode and a second electrode of the plurality of electrodes at respective first and second weights, the second stimulation channel corresponds to activation of the first electrode and the second electrode at respective third and fourth weights; and at least one of the weights of the first and second weights is different from at least one of the weights of the third and fourth weights. In an exemplary embodiment, the second electrode is immediately adjacent the first electrode. In an exemplary embodiment, the multichannel stimulation entails activating the first electrode and the second electrode at respective fifth and sixth weights, wherein at least one of (i) the fifth weight is different from the first and third weight or (ii) the sixth weight is different from the second and fourth weight. In an exemplary embodiment, the multichannel stimulation entails activating the first electrode and the second electrode at respective fifth and sixth weights, wherein at least one of (i) the fifth weight is the summation of the first weight and the third weight or (ii) the sixth weight is a summation of the second weight and the fourth weight. In an exemplary embodiment, the method includes identifying a second recipient specific parameter related to a second current level of the stimulating device for the first stimulation channel by instructing the stimulating device to apply the multichannel stimulation to the recipient.

In at least some embodiments, the goal of at least some of the various method actions and/or methods detailed herein and/or variations thereof is to obtain a fitted electrical stimulation device having performance characteristics that are based on the results of the methods. Accordingly, in an exemplary embodiment, the methods detailed herein and/or variations thereof enable a cochlear implant to apply electrical stimulation based on multiple channels (including all channels of the cochlear implant) simultaneously, and thus enable the creation (by way of fitting) of a cochlear implant having such functionality. In an exemplary embodiment, the actions of simultaneous applying electrical stimulation based on multiple/all channels are executed in a manner that takes into account the fact that there will be residual interactions between channels (e.g., at least neighboring channels with respect to the stimulation strategies of the '301 publication). By way of example only and not by way of limitation, such can be achieved by fitting a cochlear implant according to the teachings detailed herein and/or variations thereof. For example, by developing and/or utilizing merged channels to fit target channels to a given recipient, where the merged channels are combinations of channels that interact with one another developed in accordance with the teachings detailed herein and/or variations thereof, the stimulations used during the fitting process more closely correspond to the stimulations that would occur during autonomous operation of the cochlear implant in a simultaneous channel stimulation regime, where there is residual channel interaction.

By using the hybrid channels in the fitting process, standard fitting methodologies can be utilized to obtain T and C levels, etc., and then the cochlear implant can be utilized during autonomous operation with the T and C levels obtained based on the hybrid channels.

Accordingly, in an exemplary embodiment, there is a cochlear implant that has been fitted to a recipient based on the hybrid channels detailed herein, such that the T and C levels of the cochlear implant take into account residual channel interactions that results from simultaneous stimulation based on multiple (including all) channels, thus enabling the cochlear implant to simultaneously apply stimulation based on multiple (including all) channels.

Figure 10:
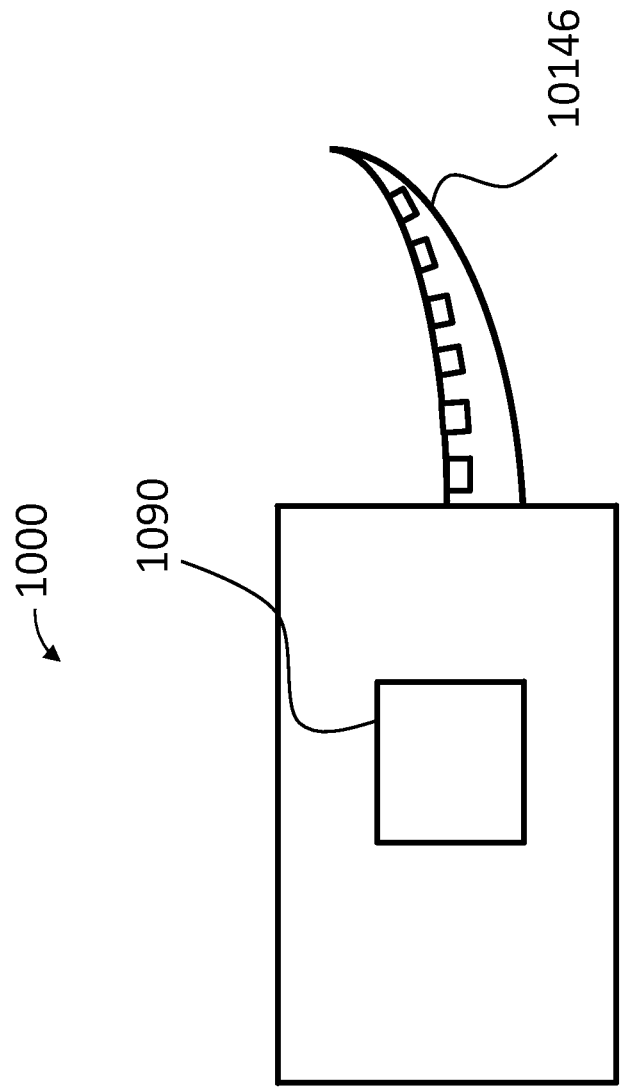
FIG. 10 presents an exemplary electrical stimulation device in the form of a cochlear implant according to an exemplary embodiment.

In this regard, in an exemplary embodiment, there is an electrical stimulation device, such as by way of example, a cochlear implant, that is fitted to a recipient. FIG. 10 presents a functional diagram of such a cochlear implant 1000, functionally corresponding to cochlear implant 100 detailed above.

As can be seen, the cochlear implant 1000 includes an electrode array 10146 (corresponding to the electrode array 146 detailed above with respect to FIG. 1) that includes a plurality of electrodes. As with the cochlear implant 100 detailed above, the cochlear implant 1000 is configured for implantation into a recipient and to apply electrical stimulation to the recipient by activating one or more of a plurality of electrode channels of the cochlear implant 1000 to evoke a hearing percept.

In the embodiment of FIG. 10, the cochlear implant 1000 includes a control unit 1090 that is configured to control the cochlear implant 1000 to apply electrical stimulation to the recipient by activating a first electrode channel of the plurality of electrode channels to evoke a hearing percept at current levels within a range bounded by at least one of a threshold level or a comfort level. In the exemplary embodiment of FIG. 10, at least one of the respective threshold level current level or comfort level current level is based on empirical data that is based on at least one of a recipient specific respective threshold level or comfort level obtained by simultaneously activating the first electrode channel and a second electrode channel of the plurality of electrode channels. In an exemplary embodiment, this empirical data is obtained by executing one or more or all of the method actions detailed herein and/or variations thereof.

In an exemplary embodiment of the device of FIG. 10, the control unit 1090 is configured to control the cochlear implant to apply electrical stimulation to the recipient by activating the first electrode channel to evoke a hearing percept at current levels within a range bounded respectively by the threshold level and the comfort level, wherein the threshold level current level and comfort level current level are based on empirical data that is based on, respectively, recipient specific threshold level and comfort level obtained by simultaneously activating the first electrode channel and the second electrode channel. In an exemplary embodiment, at least one of the threshold or comfort levels is based on empirical data that is based on at least one of a recipient specific respective threshold level or comfort level obtained by simultaneously activating the first electrode channel, the second electrode channel and a third electrode channel of the plurality of electrode channels. In at least some exemplary embodiments, the empirical data is obtained by executing one or more or all of the method actions detailed herein and or variations thereof.

In an exemplary embodiment, the aforementioned second electrode channel and/or the aforementioned third electrode channel is/are electrode channel(s) that interact(s) with the first electrode channel when the first and second and/or third electrode channels are activated during operation of the cochlear implant to evoke a hearing percept. By way of example only and not by way of limitation, the interaction can correspond to the interaction detailed in the '301 publication detailed above.

Still further, by way of example only and not by way of limitation, in an exemplary embodiment, the control unit 1090 is configured to control the cochlear implant to apply electrical stimulation to the recipient by activating the first electrode channel to evoke a hearing percept at current levels within a range bounded by the threshold level and the comfort level, wherein the threshold level and the comfort level are based on empirical data that is based on, respectively, recipient specific threshold and comfort levels obtained by simultaneously activating the first electrode channel and all electrode channels that interact with the first electrode channel during operation of the cochlear implant to evoke a hearing percept.

It is noted that in at least some embodiments, the recipient specific parameters (e.g. threshold level, comfort level, etc.), can be ascertained via subjective methods, which can include affirmative indications by the recipient with regard to the recipient specific parameters (e.g., the recipient can state that the resulting hearing percept is too loud and/or that an applied current level does not result in a hearing percept's, etc.). Alternatively and/or in addition to this, the recipient specific parameters can be ascertained via objective methods, which can include utilizing electrically evoked compound action potentials (ECAPs) or other brain evoked potentials. By way of example only and not by way of limitation, in some exemplary embodiments, there includes a method entailing interrogating the performance of the cochlear implant and making objective measurements of recipient specific data such as T and C levels, etc., by directly measuring the response of the auditory nerve to an electrical stimulus resulting from the cochlear implant 100. The measurement of the ECAPS can provide an objective measurement of the response of the nerves to electrical stimulus. In at least some exemplary embodiments, following electrical stimulation, the neural response is caused by the superposition of single neural responses at the outside of the axon membranes. The ECAP is then measured in response to various stimulations and from this the performance of the cochlear implant can be assessed and recipient parameters can be interpolated.

Any device, system and/or method that can enable the recipient specific parameters to be ascertained or otherwise estimated to enable the teachings detailed herein can be utilized in at least some embodiments.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
    fitting an electrical stimulating device to a recipient, the electrical stimulating device including electrodes implanted in the recipient, the electrical stimulating device being a multipolar electrical stimulating device, wherein the fitting includes:
        simultaneously applying multipolar stimulation to the recipient via the electrodes based on at least two different multipolar stimulation channels of the electrical stimulating device; and
        determining a threshold level specific to the recipient based on the simultaneously applied multipolar stimulation channels.

2. The method of claim 1, wherein:
    the electrical stimulating device is configured to apply electrical stimulation to the recipient via the electrodes by activating a plurality of stimulation channels, and the method further comprises:
        identifying one of the stimulation channels as a target channel; and
        identifying a plurality of interacting stimulation channels of the plurality of stimulation channels that interact with the target stimulation channel of the plurality of stimulation channels during autonomous operation of the stimulating device, wherein the identified at least one interacting stimulation channels are different from the target channel.

3. The method of claim 2, wherein:
    the action of identifying the plurality of interacting stimulation channel includes identifying all interacting stimulation channels that at least substantially interact with the target stimulation channel during autonomous operation of the stimulating device.

4. The method of claim 1, wherein:
    the action of simultaneously applying multipolar stimulation to the recipient via the electrodes based on at least two different multipolar stimulation channels of the electrical stimulating device does not include an action of applying multipolar stimulation to the recipient utilizing only a single stimulation channel.

5. The method of claim 1, wherein the action of fitting the electrical stimulating device includes:
    fitting a hearing prosthesis.

6. The method of claim 1, further comprising:
    developing a first stimulation channel;
    developing a second stimulation channel;
    developing a third stimulation channel, wherein the at least two different stimulation channels include at least the first stimulation channel, the second stimulation channel and the third stimulation channel;
    identifying one of the first, second or third stimulation channels as a target channel; and
    combining the first, second and third stimulation channels to make up a merged channel, wherein
    the applied simultaneous multipolar stimulation corresponds to the merged channel.

7. The method of claim 6, wherein:
    the merged channel does not include any other channels other than the first, second and third channels.

8. The method of claim 6, further comprising:
    developing a fourth simulation channel, wherein
    the merged channel does not include the fourth channel.

9. The method of claim 6, wherein:
    the first stimulation channel is the target channel; and
    the second and third stimulation channels are channels that interact with the target channel.

10. The method of claim 7, further comprising:
    fitting the electrical stimulating device to the recipient, wherein the electrical stimulating device is configured to apply electrical stimulation to the recipient by simultaneously activating a plurality of electrode channels of the device to evoke a hearing percept, wherein the device is configured to:
        control the device to apply electrical stimulation to the recipient by activating the first stimulating channel to evoke a hearing percept at current levels within a range bounded by at least one of a threshold level or a comfort level, wherein
        at least one of the respective threshold level current level or comfort level current level is based on empirical data that is based on the action of applying simultaneous multipolar stimulation.

11. The method of claim 9, wherein:
    the electrical stimulating device is configured to apply electrical stimulation to the recipient via the electrodes by activating a plurality of the stimulation channels; and
    the method further comprises identifying a plurality of interacting stimulation channels of the plurality of stimulation channels that interacts with the target stimulation channel of the plurality of stimulation channels during autonomous operation of the stimulating device, wherein the identified at least one interacting stimulation channels are the second and third stimulation channels.

12. The method of claim 11, wherein:
    the stimulation channels have respective weights for respective electrodes of the electrodes; and
    the action of combining the first and second and third stimulation channels to make up the merged channel includes summing respective electrode weights for the interacting stimulation channels and respective electrode weights for the target stimulation channel.

13. The method of claim 11, wherein:
    the action of identifying the plurality of interacting stimulation channel includes identifying all interacting stimulation channels that at least substantially interact with the target stimulation channel during autonomous operation of the stimulating device.

14. The method of claim 11, wherein:
the target channel is a first target channel and the plurality of interacting stimulation channels is an at least one first interacting stimulation channel that includes a plurality of channels; and
the method further comprises:
identifying at least one second interacting stimulation channel of the plurality of stimulation channels that interacts with a second target stimulation channel of the plurality of stimulation channels;
creating a second merged channel based on the identified at least one second interacting stimulation channel and the second target stimulation channel;
activating the second merged channel to evoke a stimulation induced percept; and
setting at least one of a threshold level or a comfort level for the second target stimulation channel based on activation of the second merged channel.

15. The method of claim 14, wherein:
one of the at least one first interacting stimulation channels is the second target channel; and
one of the at least one second interacting stimulation channels is the first target channel.

16. The method of claim 15, wherein:
identifying at least one third interacting stimulation channel of the plurality of stimulation channels that interacts with a third target stimulation channel of the plurality of stimulation channels;
creating a third merged channel based on the identified at least one third interacting stimulation channel and the third target stimulation channel;
activating the third merged channel to evoke a stimulation induced percept; and
setting at least one of a threshold level or a comfort level for the third target stimulation channel based on activation of the third merged channel, wherein
none of the third interacting stimulation channel(s) substantially interact with the first target stimulation channel during autonomous operation of the stimulating device.

17. A method, comprising:
fitting an electrical stimulating device to a recipient, the electrical stimulating device including electrodes implanted in the recipient, the electrical stimulating device being a multipolar electrical stimulating device, wherein the fitting includes:
simultaneously applying multipolar stimulation to the recipient via the electrodes based on at least two different multipolar stimulation channels of the electrical stimulating device,
wherein the method further comprises:
developing a first stimulation channel;
developing a second stimulation channel, wherein the at least two different stimulation channels include at least the first stimulation channel and the second stimulation channel;
identifying one of the first or second stimulation channels as a target channel; and
combining the first and second stimulation channels to make up a merged channel, wherein
the applied simultaneous multipolar stimulation corresponds to the merged channel.

18. The method of claim 17, wherein the action of fitting the stimulating device includes:
determining a comfort level specific to the recipient based on the simultaneously applied multipolar stimulation channels.

19. The method of claim 17, wherein:
the first stimulation channel is the target channel; and
the second stimulation channel is a channel that interacts with the target channel.

20. The method of claim 17, wherein:
the electrical stimulating device is configured to apply electrical stimulation to the recipient by simultaneously activating a plurality of electrode channels of the device to evoke a hearing percept, wherein the device is configured to:
control the device to apply electrical stimulation to the recipient by activating the first stimulating channel of the at least two different stimulation channels to evoke a hearing percept at current levels within a range bounded by at least one of a threshold level or a comfort level, wherein
at least one of the respective threshold level current level or comfort level current level is based on empirical data that is based on the action of applying simultaneous multipolar stimulation.

21. The method of claim 17, wherein:
the first stimulation channel is the target channel; and
the second stimulation channel is a stimulation channel that interacts with the target stimulation channel at least at supra threshold levels when the interacting stimulation channel is activated at the same time as the target stimulation channel.

22. The method of claim 17, wherein:
the first stimulation channel is the target channel; and
the second stimulation channel is a stimulation channel that influences the target channel due to current spread to a first electrode of the target stimulation channel from a second electrode of the second stimulation channel, the first and second electrodes being at least some of the electrodes implanted in the recipient.

23. The method of claim 17, wherein:
the first stimulation channel is the target channel;
the second stimulation channel is a channel that interacts with the target channel; and
there is only one channel interacting with the target channel.

24. The method of claim 17, wherein:
the first stimulation channel is the target channel;
the second stimulation channel is a channel that interacts with the target channel; and
there is only one other stimulation channel interacting with the target channel in addition to the second stimulation channel.

25. A method, comprising:
fitting an electrical stimulating device to a recipient, the electrical stimulating device including electrodes implanted in the recipient, the electrical stimulating device being a multipolar electrical stimulating device, wherein the fitting includes:
applying multipolar stimulation to the recipient via the electrodes based on at least two different multipolar stimulation channels of the electrical stimulating device; and
determining a threshold level specific to the recipient based on the applied multipolar stimulation channels.

26. The method of claim 25, wherein:
the action of applying multipolar stimulation to the recipient via the electrodes based on at least two different multipolar stimulation channels includes simultaneously applying multipolar stimulation to the recipient via the electrodes based on at least two different multipolar stimulation channels of the electrical stimulating device.

27. The method of claim 25, wherein the action of fitting the stimulating device includes:
fitting a hearing prosthesis, and wherein the method further includes capturing sound, converting the captured sound into electrical stimulation and applying the electrical stimulation using the stimulation device to evoke a hearing percept based on the captured sound.

28. A method, comprising:
fitting an electrical stimulating device to a recipient, the electrical stimulating device including electrodes implanted in the recipient, the electrical stimulating device being a multipolar electrical stimulating device, wherein the fitting includes:
applying multipolar stimulation to the recipient via the electrodes based on at least two different multipolar stimulation channels of the electrical stimulating device,
wherein the electrodes are part of an electrode array having an elongate carrier and separate electrodes carried by the carrier arrayed along a length of the array, the electrode carrier and the electrodes being located in a cochlea of a person.

29. The method of claim 28, wherein the action of fitting the stimulating device includes:
determining a comfort level specific to the recipient based on the applied multipolar stimulation channels.

30. The method of claim 28, wherein:
the action of applying multipolar stimulation to the recipient via the electrodes based on at least two different multipolar stimulation channels includes serially applying multipolar stimulation to the recipient via the electrodes based on at least two different multipolar stimulation channels of the electrical stimulating device.

31. The method of claim 28, further comprising:
developing a first stimulation channel;
developing a second stimulation channel;
developing a third stimulation channel, wherein the at least two different stimulation channels include at least the first stimulation channel, the second stimulation channel and the third stimulation channel;
identifying one of the first, second or third stimulation channels as a target channel; and
combining the first, second and third stimulation channels to make up a merged channel, wherein
the applied simultaneous multipolar stimulation corresponds to the merged channel.

32. The method of claim 31, wherein:
the first stimulation channel is the target channel; and
the second and third stimulation channels are channels that interact with the target channel.

33. The method of claim 32, wherein:
the action of applying multipolar stimulation to the recipient via the electrodes based on at least two different multipolar stimulation channels includes simultaneously applying multipolar stimulation to the recipient via the electrodes based on at least two different multipolar stimulation channels of the electrical stimulating device.

34. The method of claim 32, wherein:
the action of applying multipolar stimulation to the recipient via the electrodes based on at least two different multipolar stimulation channels includes serially applying multipolar stimulation to the recipient via the electrodes based on at least two different multipolar stimulation channels of the electrical stimulating device.

* * * * *